United States Patent [19]
Platz et al.

[11] 3,934,147
[45] Jan. 20, 1976

[54] PATIENT SUPPORT WITH WEIGHT-SENSITIVE SPRING SCALE FOR CONTROLLING MOTOR OPERATION

[75] Inventors: Winfried Platz, Rathsberg; Ulrich Bar, Nurnberg; Martin Schmidt, Eltersdorf, all of Germany

[73] Assignee: Siemens Aktiengesellschaft, Munich, Germany

[22] Filed: Feb. 8, 1974

[21] Appl. No.: 440,708

[30] Foreign Application Priority Data
Feb. 13, 1973   Germany............................. 2307044

[52] U.S. Cl. .................. 250/445; 177/48; 250/449
[51] Int. Cl. .......................................... G01n 23/00
[58] Field of Search ........... 250/439, 442, 449, 444, 250/446, 447, 448; 269/322, 323; 177/45–48, 145, 245

[56] References Cited
UNITED STATES PATENTS

| | | | |
|---|---|---|---|
| 2,526,879 | 10/1950 | Kizaur................................ | 250/449 |
| 3,220,498 | 11/1965 | DeParo et al......................... | 177/48 |
| 3,329,224 | 7/1967 | Waters.................................. | 177/48 |
| 3,550,703 | 12/1970 | Knothe et al. ........................ | 177/45 |
| 3,822,875 | 7/1974 | Schmedemann..................... | 250/444 |

Primary Examiner—Harold A. Dixon
Assistant Examiner—D. C. Nelms
Attorney, Agent, or Firm—V. Alexander Scher

[57] ABSTRACT

A device for supporting a patient, having a carrying member and a horizontally extending lying support for the patient, with a motor for varying the distance between the support and a medicinal unit. The invention is particularly characterized by the provision of a spring scale between the patient support and its carrying member, having a switching member which can be shifted corresponding to the weight of the patient. Switching means are connected with the switching member for interrupting the current circuit of the motor, the distance between the switching means and the switching member being adjustable.

8 Claims, 5 Drawing Figures

PATIENT SUPPORT WITH WEIGHT-SENSITIVE SPRING SCALE FOR CONTROLLING MOTOR OPERATION

This invention relates to a patient supporting device with a carrying member and a horizontally extending lying support for the patient provided with a motor for varying the distance between it and a medicinal unit.

A patient supporting device of this type is used, for example, in combination with a gamma camera for determining the distribution of radioactive substances in the body of a patient. For that purpose it is necessary to be able to adjust the distance between the collimator of the gamma camera and the patient in such manner that the collimator can be placed directly at the surface of the patient. Then there is the danger that the patient will be squeezed between the lying support and the gamma camera.

The German patent specification No. 1,960,625 discloses a protecting device for a medicinal or dental unit, consisting of a height-adjustable or fixed bracket of a treating device and a device for carrying a patient. In order to prevent the squeezing of a patient between the bracket and the carrying device, an electronic switch is provided which prevents all contact with the patient. Its actuating distance is either fixed or variable and it can interrupt the current circuit of the motor operating the height adjustment. However, such a protecting device can not be used in all cases, particularly not in an isotope diagnosing device. In an isotope diagnosing device it is necessary, as already stated, that the gamma camera should be movable so close to the patient that it can touch him. On the other hand, it must provide measurements under different angles. For that purpose it is mounted so as to be swingable about a horizontal axis and so that it can be moved to the patient under different angles. A protecting switch which would prevent all contact with the patient can not be used. A switching strip which could replace such a protecting switch is also not useable, since it also does not act upon the patient in all positions of the gamma camera and does not permit a direct contact of the collimator of the gamma camera with the patient.

An object of the present invention is to provide a patient supporting device of the described type which, on the one hand, positively prevents the appearance of improper high forces between a patient and a medical unit and, on the other hand, makes possible a contact between the medical unit and the surface of a patient.

Other objects of the present invention will become apparent in the course of the following specification.

In the accomplishment of the objectives of the present invention it was found desirable to provide a spring scale between the patient's support and its carrying member with a switching member which can be shifted corresponding to the weight of the patient; furthermore, switching means are connected with the switching member for interrupting the current circuit of the motor, the distance between the switching means and the switching member being adjustable.

It is of importance for the subject of the present invention that the spring scale should be so dimensioned or made so adjustable that the motor will stand still in case of a predetermined force exerted upon the support and adjusted to the weight of the patient. Independent from the patient's weight, forces can be exerted upon the patient within a predetermined range. The motor will be stopped when the predetermined force acting upon the patient is exceeded. This force is given by the measure of the spring scale or by the distance between the switching member and the switching means.

According to a practical embodiment of the present invention, the switching means are frictionally connected with a guide and interrupt the current circuit of the motor in their initial position. To free the shifting they are pressed manually by an actuating member from the initial position toward the switching member. In this embodiment of the invention the force which when exceeded will stop the motor is determined by the sizing of the spring scale.

Within the scope of the present invention, the motor which changes the distance between the patient's support and the medical unit can be either an adjusting motor for the patient's support or an adjusting motor for the medical unit.

The invention will appear more clearly from the following detailed description when taken in connection with the accompanying drawings showing by way of example only, a preferred embodiment of the inventive idea.

Figure 1:
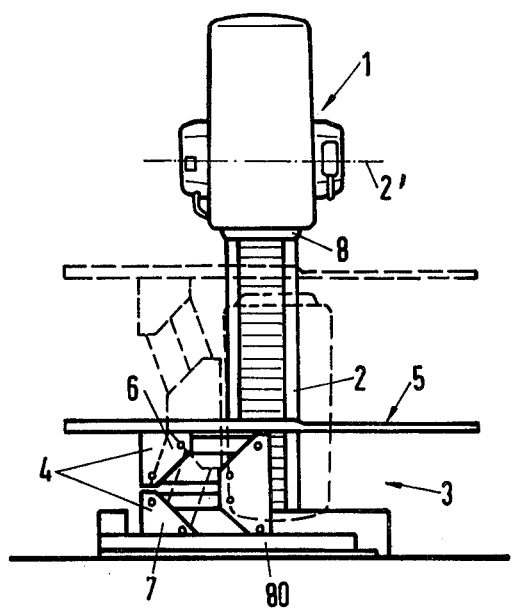
FIG. 1 is a side view of a patient supporting device of the present invention combined with a gamma camera.

FIG. 1 shows a gamma camera 1 which is adjustable in height upon a stand 2. The gamma camera is swingable about different axes, including the horizontal axis 2' shown in FIG. 1. A patient supporting device 3 combined with the gamma camera 1 consists of a carrying member 4 mounted upon the floor and a patient support 5. The carrying member 4 is shaped as a double parallelogram. The patient support 5 is connected with the upper holding head 6 of this double parallelogram, while the lower holding head 7 is fixed to a socket 80.

The patient lying upon the support can be raised by a motor-operated height shifting device connected with the support up to the collimator 8 of the gamma camera 1. However, when the patient is immovable the gamma camera 1 with the collimator 8 can be moved by motor to the body surface of the patient.

Figure 2:
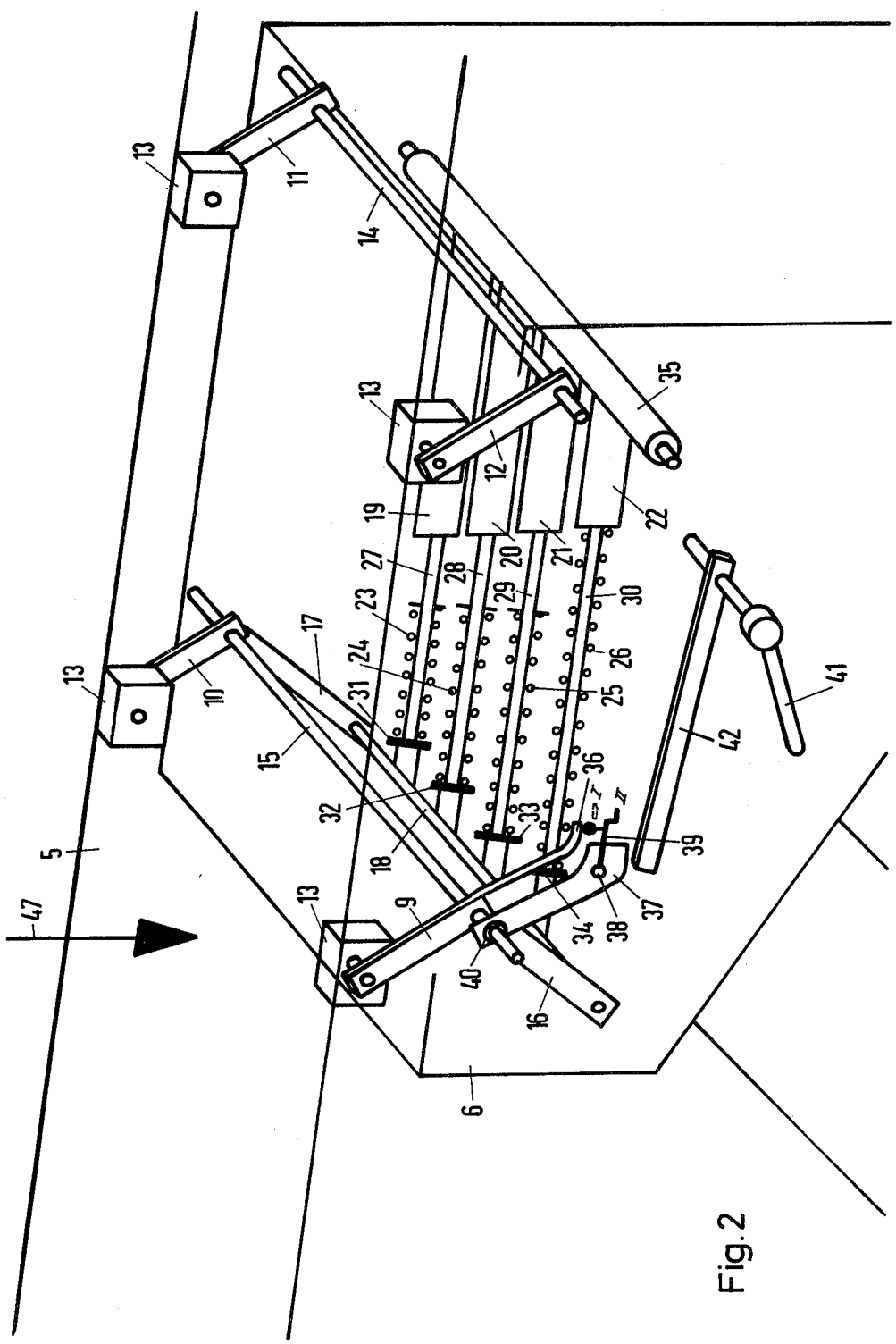
FIG. 2 is a diagrammatic perspective view showing parts of the patient supporting device of FIG. 1 which are important for the present invention.

FIG. 2 shows that the patient support 5 is connected by a spring scale with the holding head 6. This spring scale includes a parallelogram rod connection with four levers 9 to 12 which on the one hand are swingably mounted in pedestals 13 fixed to the patient support 5, and on the other hand, are swingable about two shafts 14 and 15 which are fixed in the holding head 6. The levers 9 and 10 have two angularly shifted beams 16 and 17 interconnected by a rod 18. Between the rod 18 and four stops 19 to 22, four pressure springs 23 to 26 are guided. For that purpose are used four rods 27 to 30 upon which the springs 23 to 26 are shifted. Four stops 31 and 34 connected with the rod 18 act upon the left hand end of the springs 23 to 26, so that the stops 31 to 34 can be resiliently supported against stops 19 to 22. For that purpose the stops 31 to 34 are shiftable sleeve-like upon the rods 27 to 30. The stops 19 to 22 are fixed upon a shaft 35 swingable in the holding head 6.

A bracket 36 firmly connected with the lever 9 and cooperating with a lever 37 serves as a switching member. The lever 37 carries at its free end a switch 38 with an actuating member 39 and is connected with the shaft 15 by a friction coupling 40. A lever 41 extends out of the holding head 6. The lever 37 can be swung by the lever 41 through an intermediate lever 42 in the direction toward the bracket 36, so that the bracket 36 will press upon the actuating member 39.

The operation of the device of FIG. 2 is further described in connection with the basic circuit of FIG. 3.

Figure 3:
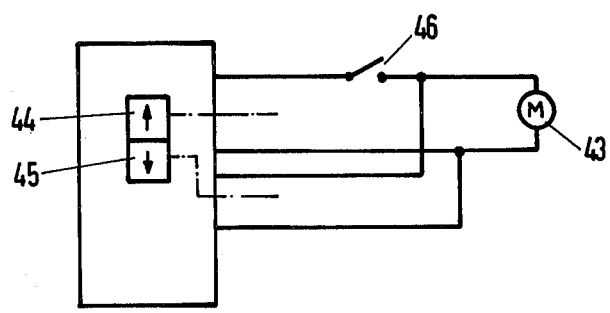
FIG. 3 is a block switch diagram showing means actuating the adjusting motor in the device of FIG. 1.

FIG. 3 shows a motor 43 which, for example, serves for the height adjustment of the patient support 5 and which can be actuated by two buttons 44 and 45 so that the patient support 5 can be raised or lowered. In front of the motor 43 is the contact 46 of the switch 38.

A downward movement of the patient support 5 is possible independently from the contact 46, namely, when the button 45 is actuated the support 5 will always move downwardly since there is no danger for the patient. However, an upward movement of the support 5 is possible only when the contact 46 is closed.

When a patient is placed upon the support 5, it will move downwardly somewhat in the direction of the arrow 47, whereby one or several springs 23 to 26 will be compressed corresponding to the weight of the patient. The bracket 36 will move a distance relatively to the level 37 and thus also to the actuating member 39, which corresponds to the weight of the patient.

The actuating member 39 will assume initially the position I in which the switch 46 is opened due to the distance between the member 39 and the bracket 36. When a patient is placed upon the support 5 thus it will not be able to move upwardly. To provide an upward movement the operator will swing clockwise the lever 41, whereby the lever 42 will swing the lever 37 counterclockwise until the actuating member 39 lies upon the bracket 36 and is moved into the position II. After the lever 41 is released the lever 37 and the actuating member 39 keep this position due to the frictional connection between the shaft 15 and the lever 47.

In the position II the contact 46 is closed, so that the patient then can be moved upwardly.

If a force acts upon the patient support 5 in the direction of the arrow 47, which exceeds by a predetermined amount the weight of the patient, then the distance between the holding head 6 and the patient support 5 is somewhat diminished while one or several of the springs 23 to 26 are compressed, whereby the bracket 36 is removed from the actuating member 39. The actuating member 39 swings into its position I and opens the contact 46, so that the motor is switched off for the upward movement of the support 5.

The springs 23 to 26 are so measured that in a predetermined range of patient's weight, for example, from 30 to 135 kp, the path of movement of the bracket 36 in case of an increase of a specific patient's weight by a predetermined amount, for example, 3 kp, will be always the same. This provides that when the patient's weight is higher by more than 5 kp, there is an automatic stop to the upward movement of the patient support 5. Thus if, for example, the patient strikes the collimator 8 of the gamma camera 1, the upward movement of the support 5 will stop.

The spring scale between the patient support 5 and the holding head 6 has the advantage that the collimator 8 can be moved to the patient until it touches him without a switchoff. The motor for the high movement of the support 5 is stopped only when an improperly high force acts upon the patient. The spring scale has also the advantage that an unavoidable running of the motor after it has been switched off will not damage the patient, since the support 5 can give in relatively to the holding head 6.

The present invention makes possible a simple adjustment to the actual weight of the patient by operating the lever 41. Moreover, within the scope of the present invention, it is also possible to use a stop adjustable relatively to the bracket 36, while accepting an additional difficulty in the mounting. Thus stop would be adjustable in such manner that for each patient a precisely predetermined distance between these two parts would be set, the bracket 36 causing the stoppage of the motor after it is overcome. Consequently, a predetermined distance must be set manually in this case which would correspond to a specific force exceeding the patient's weight of, for example, 5 kp, whereby after it is reached the upward movement of the carrier 5 is switched off.

The present invention has been described in connection with a patient supporting device which is adjustable in height by a motor and wherein the motor raising the patient support can be automatically stopped. Moreover, within the framework of the present invention the motor 43 can be also a motor which moves downwardly the gamma camera 1. In that case the gamma camera 1 will be stopped with the same precision when the force upon the patient exceeds a predetermined amount. In that case the buttons 44 and 45 must be exchanged.

Figure 4:
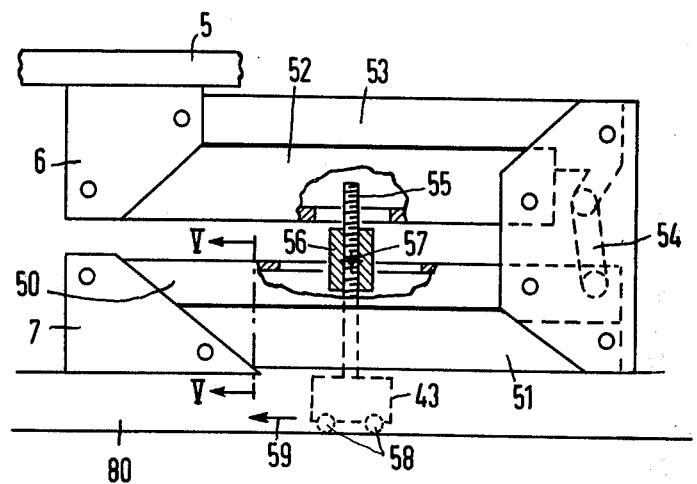
FIG. 4 shows in side view and partly in section and on an enlarged scale the adjusting mechanism for the patient's support.
Figure 5:
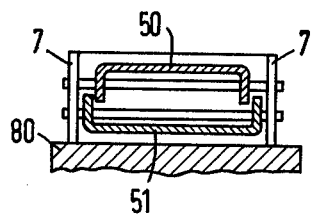
FIG. 5 is a section along the line V—V of FIG. 4.

As shown in FIGS. 4 and 5 the adjusting mechanism for the patient support 5 includes four parallel guides 50 to 53. The parallel guides 50 and 51 consist of U-shaped profiles, whereby the open U sides extend toward each other, so that the two profiles interengage. The parallel guides 52 and 53 are shaped in the same manner. The holding heads 6 and 7 are also U-shaped so that the parallel guides 50 to 53 can engage between these holding heads. In this construction the rodes are closed from all sides so that there can be no accidents caused by unintentional engagement.

FIG. 4 shows that to provide power transmission between the two parallelogram rods, the parallel guide 50 and the parallel guide 53 are pivotally interconnected by a guide 54. The movement of the patient support 5 takes place by the motor 43 through a threaded rod 55 which is guided in a guide screw 56. The guide screw 56 is connected with the parallel guide 50 and is swingable about an axis 57. When the motor 43 turns the threaded rod 55, the parallel guide 50 as well as the parallel guide 51 will be shifted, and also the parallel guides 52 and 53 through the guide 54. The shifting takes place in such manner that the patient support 5 will be moved vertically upwardly from the illustrated initial position. The motor 43 is movably guided in the direction of the arrow 59 by wheels 58 and rails in the pedestal 80, so that the movements of the guiding screw 56 can be balanced in a horizontal direction.

What is claimed is:
1. A device for supporting a patient for use with a medical apparatus, said device comprising a carrying member, a substantially horizontally extending support for the patient, a motor for varying the distance be- tween said support and said medical unit, a supply circuit for said motor, and a spring scale between said support and said carrying member, said spring scale having a switching member shiftable depending upon the weight of a patient, said switching member having switching means for interrupting said supply circuit for said motor and means adjusting the distance of said switching means from said switching member.

2. A device in accordance with claim 1, comprising parallelogram rods supporting said support upon said carrying member, and spring means engaging said rods.

3. A device in accordance with claim 1, wherein said motor serves for the movement of said medical unit.

4. A device in accordance with claim 1, wherein said medical unit is a gamma camera.

5. A device in accordance with claim 1, wherein said motor serves for the movement of said support in a vertical direction.

6. A device in accordance with claim 1, comprising a guide fixed upon an upper portion of said carrying member, said switching means being frictionally connected with said guide, and a manually operable actuating member, said switching means interrupting said supply circuit in a basic position and being pressable by said actuating member against said switching member for being switched out of said basic position, thereby freeing the upward movement of said support.

7. A device in accordance with claim 6, wherein said switching member is a switch lever, and wherein said switching means consist of a switch and another lever carrying said switch and having a swinging axle, said device comprising a friction coupling located between said other lever and said swinging axle.

8. A device in accordance with claim 6, wherein said spring characteristic is such that switching member always moves by the same distance for a predetermined force added to any weight of a patient.

* * * * *